United States Patent
Rieke-Zapp et al.

(10) Patent No.: US 8,053,590 B2
(45) Date of Patent: Nov. 8, 2011

(54) METHOD FOR PRODUCING ENANTIOMERIC FORM OF 2,3-DIAMINOPROPIONIC ACID DERIVATIVES

(75) Inventors: Joerg Rieke-Zapp, Frankfurt (DE); Guenter Billen, Niedernhaussen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 35 days.

(21) Appl. No.: 12/418,737

(22) Filed: Apr. 6, 2009

(65) Prior Publication Data
US 2009/0203918 A1    Aug. 13, 2009

Related U.S. Application Data

(60) Division of application No. 11/621,654, filed on Jan. 10, 2007, now Pat. No. 7,514,578, which is a continuation of application No. PCT/EP2005/006920, filed on Jun. 28, 2005.

(30) Foreign Application Priority Data

Jul. 10, 2004   (DE) .................. 10 2004 033 406

(51) Int. Cl.
 *C07C 229/00* (2006.01)
(52) U.S. Cl. .............. 560/37; 560/24; 560/27
(58) Field of Classification Search .............. None
See application file for complete search history.

(56) References Cited

U.S. PATENT DOCUMENTS 7,285,560 B2 * 10/2007 Ritzeler et al. ............ 514/275
2005/0197353 A1   9/2005 Ritzeler et al.

FOREIGN PATENT DOCUMENTS

| WO | WO 93/09173 | 5/1993 |
|----|----|----|
| WO | WO 2004/022553 | 3/2004 |
| WO | WO 2004022553 A1 * | 3/2004 |
| WO | 2005/113544 A1 | 12/2005 |

OTHER PUBLICATIONS

Andrea J. Robinson et al., Highly Enantioselective Synthesis of alpha-Beta-Diaminopropanoic Acid Derivatives Using a Catalytic Asymmetric Hydrogenation Approach, J. Org. Chem. (2001, pp. 4141-4147, vol. 66.

Japanese Office Action dated Mar. 29, 2011 together with English translation.

* cited by examiner

*Primary Examiner* — Sudhakar Katakam
(74) *Attorney, Agent, or Firm* — James W. Bolcsak; Scully, Scott, Murphy & Presser, P.C.

(57) ABSTRACT

The invention relates to a method for producing enantiomers form of 2,3-diaminopropionic acid derivatives of formula (I) by asymmetric hydrogenation from compounds of formula (II).

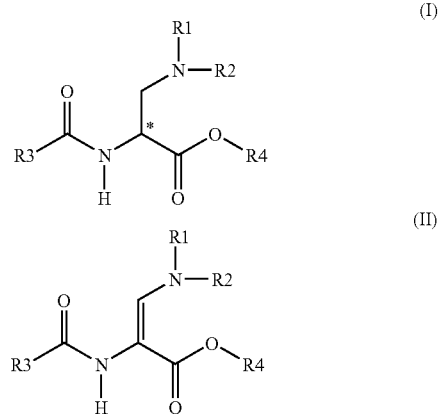

16 Claims, No Drawings

METHOD FOR PRODUCING ENANTIOMERIC FORM OF 2,3-DIAMINOPROPIONIC ACID DERIVATIVES

CROSS REFERENCE TO RELATED APPLICATIONS

This application is a divisional of U.S. application Ser. No. 11/621,654, filed on Jan. 10, 2007, which claims the benefit of priority from International Application No. PCT/EP2005/006920 filed on Jun. 28, 2005, from which the present application is a continuation, which claims the benefit of priority from German Application No. 10 2004 033 406.4, filed on Jul. 10, 2004.

FIELD OF INVENTION

The invention relates to a process for preparing the enantiomeric forms of 2,3-diaminopropionic acid derivatives of the formula I by asymmetric hydrogenation. The compounds of the formula I are suitable intermediates for preparing IkB kinase inhibitors (WO 01/30774 A1; WO 2004/022553).

BACKGROUND OF THE INVENTION

It is known that α,β-diaminopropionic acid derivatives can be prepared by Rh-catalyzed asymmetric hydrogenation according to Scheme 1 (J Org Chem, Vol. 66, 11, 2001, pages 4141-4147). However, the asymmetric hydrogenation succeeds only when both nitrogen atoms have been acylated.

Scheme 1

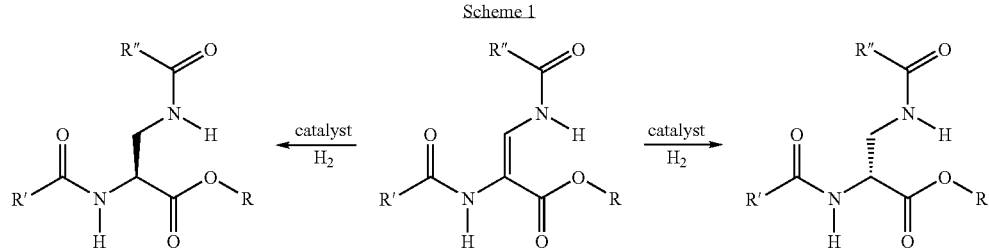

The attempt to hydrogenate N,N-dimethyleneamines or N,N-dimethylene-enamines was without success.

DETAILED DESCRIPTION OF THE INVENTION

It has now been found that the asymmetric synthesis succeeds even for compounds of the formula II. The synthesis of the compound of the formula I succeeds with high yields and high enantioselectivity.

The invention therefore relates to a process for obtaining the compound of the formula I

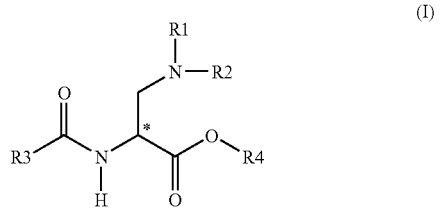

(I)

where R1 and R2 are the same or different and are each independently
1) a hydrogen atom,
2) —$(C_1$-$C_4)$-alkyl,
3) —$(C_6$-$C_{14})$-aryl where aryl is unsubstituted or mono-, di- or trisubstituted independently by R11,
where R11 is
a) F, Cl, I or Br,
b) —$(C_1$-$C_4)$-alkyl,
c) —CN,
d) —$CF_3$,
e) —$OR^5$ in which $R^5$ is a hydrogen atom or —$(C_1$-$C_4)$-alkyl,
f) —$N(R^5)$—$R^6$ in which $R^5$ and $R^6$ are each independently a hydrogen atom or —$(C_1$-$C_4)$-alkyl,
g) —$C(O)$—$R^5$ in which $R^5$ is a hydrogen atom or —$(C_1$-$C_4)$-alkyl, or
h) —$S(O)_x$—$R^5$ in which x is the integer zero, 1 or 2, and $R^5$ is a hydrogen atom or —$(C_1$-$C_4)$-alkyl,
4) —CH(R7)-aryl in which aryl is unsubstituted or mono-, di- or trisubstituted independently by —$NO_2$, —O—$CH_3$, F, Cl or bromine, where R7 is a hydrogen atom or —$(C_1$-$C_4)$-alkyl, or
5) a 4- to 15-membered Het ring where the Het ring is unsubstituted or mono-, di- or trisubstituted independently by —$(C_1$-$C_5)$-alkyl, —$(C_1$-$C_5)$-alkoxy, halogen, nitro, amino, trifluoro-methyl, hydroxyl, hydroxy-$(C_1$-$C_4)$-alkyl, methylenedioxy, ethylenedioxy, formyl, acetyl, cyano, hydroxycarbonyl, amino-carbonyl or —$(C_1$-$C_4)$-alkoxycarbonyl, R3 is 1) a hydrogen atom,
2) —$(C_1$-$C_4)$-alkyl,
3) —$(C_6$-$C_{14})$-aryl in which aryl is unsubstituted or mono-, di- or trisubstituted independently by —$NO_2$, —O—$(C_1$-$C_4)$-alkyl, F, Cl or bromine,
4) —O—$C(CH_3)_3$, or
5) —O—CH(R7)-aryl in which aryl is unsubstituted or mono-, di- or trisubstituted independently by —$NO_2$, —O—$CH_3$, F, Cl or bromine,
where R7 is a hydrogen atom or —$(C_1$-$C_4)$-alkyl,
R4 is 1) a hydrogen atom,
2) —$(C_1$-$C_4)$-alkyl or
3) —CH(R8)-aryl
in which R8 is a hydrogen atom or —$(C_1$-$C_4)$-alkyl,
which comprises hydrogenating a compound of the formula II

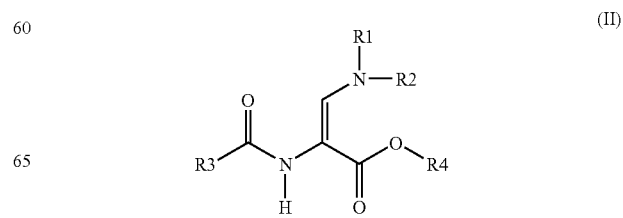

(II)

in which R1, R2, R3 and R4 are each as defined in the formula I and the compound may be present in the E or in the Z configuration on the double bond,
in the presence of hydrogen and a catalyst.

The invention further relates to a process for obtaining the compound of the formula I
where R1 is phenyl or a hydrogen atom,
R2 is phenyl, pyridyl or thiazolyl, in which phenyl, pyridyl or thiazolyl is unsubstituted or substituted by fluorine or chlorine, and
R3 is phenyl or —O—CH$_2$-phenyl and
R4 is methyl or ethyl.

The invention further relates to a process for obtaining the compound of the formula III,

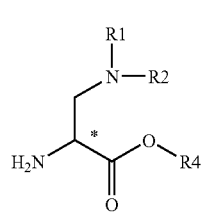

(III)

or salts thereof in which R1, R2 and R4 are each as defined in the formula I,
which comprises
a) hydrogenating the compound of the formula II

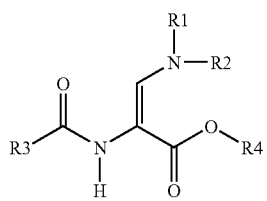

(II)

in which R1, R2, R3 and R4 are each as defined in the formula I,
in the presence of hydrogen and a catalyst, and converting it to a compound of the formula I

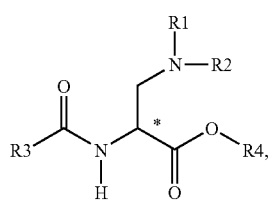

(I)

and
b) converting the resulting compound of the formula I to a compound of the formula III.

Process step b) is performed, for example, according to the reaction conditions as described by T. Greene, P. Wuts in *Protective Groups in Organic Synthesis*, Wiley-Interscience, for the cleavage of amides or carbamates. Depending on the reaction conditions selected, here strongly basic reaction conditions in particular, the direct conversion of compounds of the formula I to compounds of the formula III leads to racemization of the chiral center formed by the asymmetric hydrogenation or to other undesired side reactions. This can be prevented when the compound of the formula I is converted to the compound IV with, for example, tert-butyl dicarbonate or another reagent for the introduction of tert-butoxycarbonyl protecting groups. The tert-butoxycarbonyl protecting group is introduced in a suitable solvent such as acetonitrile, tetrahydrofuran or toluene, preferably with the aid of an acylation catalyst such as N,N-dimethylaminopyridine (DMAP). The reaction temperature is from 0° C. to 120° C., preferably from 20° C. to 40° C.

The reaction time is generally from 0.5 to 24 hours, depending on the composition of the mixture and the temperature range selected. The resulting compound of the formula IV is then converted to a compound of the formula Ia under mild conditions, such as magnesium methoxide. The conversion to the compounds of the formula III is typically done under reaction conditions known from the literature, as described by T. Greene, P. Wuts in *Protective Groups in Organic Synthesis*, Wiley-Interscience, for the cleavage of tert-butyloxycarbonyl (BOC) protecting groups.

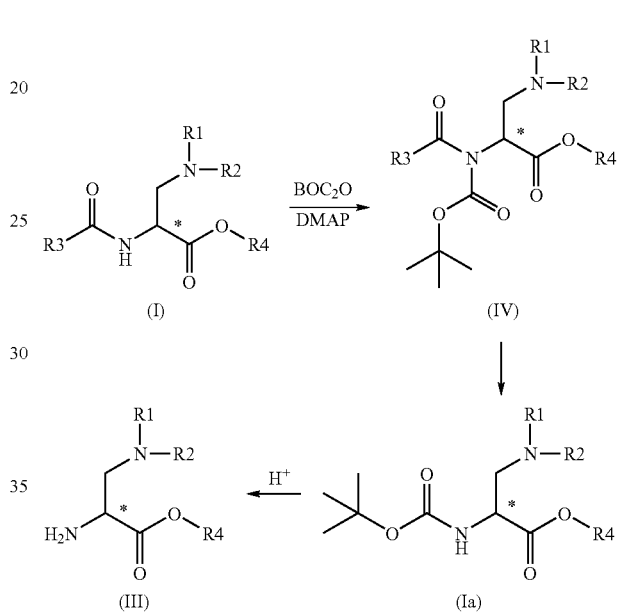

The invention therefore further relates to a process for obtaining the compound of the formula III,
which comprises
a) hydrogenating the compound of the formula II in which R1, R2, R3 and R4 are each as defined in the formula I in the presence of hydrogen and a catalyst and converting it to a compound of the formula I,
b) reacting the resulting compound of the formula I with a tert-butyl dicarbonate and an acylation catalyst such as dimethylaminopyridine (DMAP) to give a compound of the formula IV

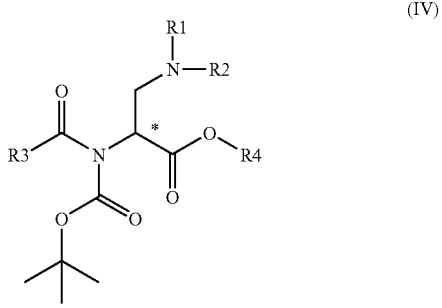

(IV)

in which R1, R2, R3 and R4 are each as defined in formula I, c) then converting the resulting compound of the formula IV to the compound of the formula Ia

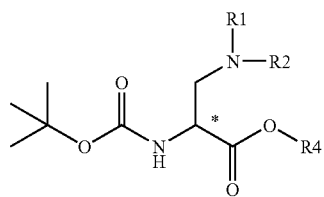
(Ia)

in which R1, R2, R3 and R4 are each as defined in formula I, and d) converting the resulting compound of the formula Ia to the compound of the formula III or salts thereof, in which R1, R2 and R4 are each as defined in formula I.

The conversion of the compounds of the formula IV to the compound of the formula Ia is achieved, for example, by treatment with bases, such as lithium hydroxide, hydrazine or magnesium methoxide (literature: J. Org. Chem. 1997, 62, 7054-7057). The tert-butyloxycarbonyl group is detached to give compounds of the formula III under standard conditions, such as treatment with trifluoroacetic acid (TFA), hydrochloric acid or p-toluenesulfonic acid in suitable solvents.

The undesired enantiomer is depleted by crystallization of the compounds of the formula I or III from suitable solvents such as methanol, ethanol, 1-propanol, 2-propanol, n-butanol, 2-butanol and esters thereof. In the case of compounds of the formula III, the crystallization is preferably performed in the form of their (acidic) salts such as hydrochloride, methanesulfonate or p-toluenesulfonate. Under these conditions, optical purities of >99% are achieved. Appropriately, the entire reaction sequence can be performed in a one-pot process without isolation of the compounds IV and Ia. The yields and optical purities achieved here correspond to the values mentioned above.

The term "catalyst" refers to compounds as described, for example, by E. N. Jacobson, A. Pfaltz, H. Yamamoto in *Comprehensive Asymmetric Catalysis*, Springer-Verlag, 1999 or X. Zhang, *Chemical Reviews*, 2003, 103, 3029-3069 and the literature cited there, for example optically active rhodium, ruthenium or iridium complexes or mixtures thereof. The catalytically active complex is formed by reaction of a metal complex with an optically active phosphine. In the case of the above-described acylated 2,3-diaminopropionic acid derivatives, the Me-Duphos or Et-Duphos-rhodium complexes exhibited very good enantioselectivities and conversions. It is also known that chiral β-amino acids can be prepared by using rhodium complexes of the BICP, t-Bu-BisP, BDPMI, Et-FerroTANE, MalPHOS and MonoPHOS type as catalysts.

The terms "—$(C_1$-$C_4)$-alkyl" or "—$(C_1$-$C_5)$-alkyl" are understood to mean hydrocarbon radicals whose carbon chain is straight-chain or branched and contains from 1 to 4 or from 1 to 5 carbon atoms, for example methyl, ethyl, propyl, isopropyl, butyl, isobutyl, tert-butyl or pentyl.

The terms "—CH(R7)-" or "—CH(R8)-" are understood to mean straight-chain or branched hydrocarbon radicals such as methylene, ethylene, isopropylene, isobutylene or pentylene. For example, in the case that R7 is a hydrogen atom and aryl is phenyl, the "—CH(R7)-aryl" radical is the benzyl radical.

The terms "—$(C_6$-$C_{14})$-aryl" or "aryl" are understood to mean aromatic carbon radicals having from 6 to 14 carbon atoms in the ring. —$(C_6$-$C_{14})$-Aryl radicals are, for example, phenyl, naphthyl, for example 1-naphthyl, 2-naphthyl, anthryl or fluorenyl. Naphthyl radicals and in particular phenyl radicals are preferred aryl radicals.

The term "4- to 15-membered Het ring" is understood to mean ring systems having from 4 to 15 carbon atoms, which are present in one, two or three ring systems bonded to one another and which contain one, two, three or four identical or different heteroatoms from the group of oxygen, nitrogen or sulfur. Examples of these ring systems are the acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl radicals.

The asterisk on a carbon atom in the compound of the formula I or II means that the particular carbon atom is chiral and that the compound is present either as the R- or S-enantiomer.

The asymmetric hydrogenation of the compounds of the formula II is advantageously performed at a temperature of from 10° C. to 200° C. and a hydrogen pressure of from 1 bar to 200 bar. The molar catalyst-reactant ratio is advantageously from 1:100 to 1:10 000.

Suitable solvents for the asymmetric hydrogenation are, for example, water, lower alcohols such as methanol, ethanol, propanol or isopropanol, aromatic hydrocarbons such as toluene, ketones such as acetone, halogenated hydrocarbons such as dichloromethane, carboxylic esters such as ethyl acetate, and ethers such as tetrahydrofuran.

The optically active 2,3-diaminopropionic acid derivatives of the formula I, III and IV as such, including in the form of their enantiomer mixtures and their salts, likewise form part of the subject matter of the present invention. Enantiomer mixtures should be understood here to mean in particular those in which one enantiomer is enriched compared to the other.

The compounds of the formula II are either known or can be prepared, for example, by reacting compounds of the formula IV in which R3 and R4 are each as defined above with an amine of the formula V in which R1 and R2 are each as defined above.

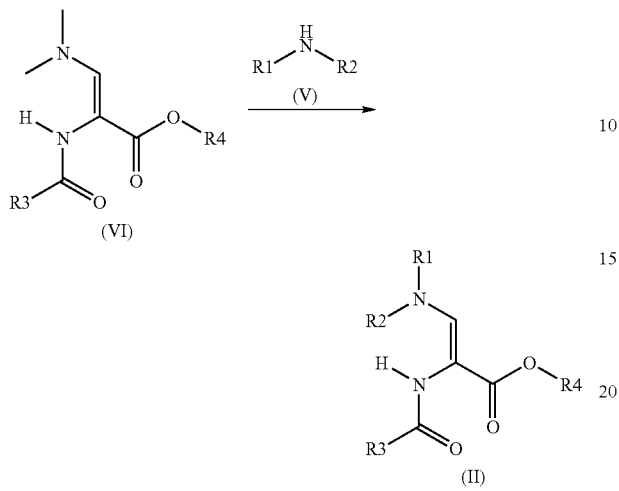

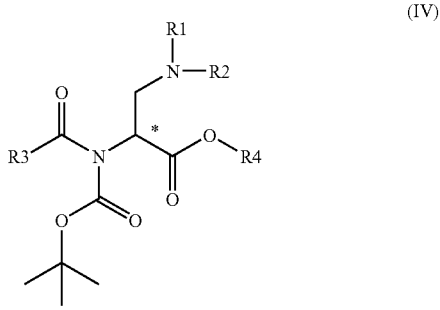

The reaction temperature is from 0° C. to 120° C., preferably from 20° C. to 60° C.

The reaction time is generally from 0.5 to 8 hours, depending on the composition of the mixture and the selected temperature range. The resulting compound of the formula II is then removed from the reaction mixture by aqueous workup and extraction with a suitable solvent, for example ethyl acetate or dichloromethane, or by crystallization.

A further aspect of the invention relates to novel compounds of the formula II where R1 and R2 are the same or different and are each independently
1) —$(C_6$-$C_{14})$-aryl where aryl is unsubstituted or mono-, di- or trisubstituted independently by R11,
where R11 is
a) F, Cl, I or Br,
b) —$(C_1$-$C_4)$-alkyl,
c) —CN,
d) —$CF_3$,
e) —$OR^5$ in which $R^5$ is a hydrogen atom or —$(C_1$-$C_4)$-alkyl,
f) —$N(R^5)$—$R^6$ in which $R^5$ and $R^6$ are each independently a hydrogen atom or —$(C_1$-$C_4)$-alkyl,
g) —$C(O)$—$R^5$ in which $R^5$ is a hydrogen atom or —$(C_1$-$C_4)$-alkyl, or
h) —$S(O)_x$—R5 in which x is the integer zero, 1 or 2, and $R^5$ is a hydrogen atom or —$(C_1$-$C_4)$-alkyl, or
2) a 4- to 15-membered Het ring where the Het ring is unsubstituted or mono-, di- or trisubstituted independently by —$(C_1$-$C_5)$-alkyl, —$(C_1$-$C_5)$-alkoxy, halogen, nitro, amino, trifluoro-methyl, hydroxyl, hydroxy-$(C_1$-$C_4)$-alkyl, methylenedioxy, ethylenedioxy, formyl, acetyl, cyano, hydroxycarbonyl, amino-carbonyl or —$(C_1$-$C_4)$-alkoxycarbonyl,
R3 is 1) —$(C_6$-$C_{14})$-aryl in which aryl is unsubstituted or mono-, di- or trisubstituted independently
by —$NO_2$, —O—$(C_1$-$C_4)$-alkyl, F, Cl or bromine,
2) —O—$C(CH_3)_3$, or
3) —O—CH(R7)-aryl in which aryl is unsubstituted or mono-, di- or trisubstituted independently
by —$NO_2$, —O—$CH_3$, F, Cl or bromine,
in which R7 is a hydrogen atom or —$(C_1$-$C_4)$-alkyl,
R4 is 1) a hydrogen atom,
2) —$(C_1$-$C_4)$-alkyl or
3) —CH(R8)-aryl
in which R8 is a hydrogen atom or —$(C_1$-$C_4)$-alkyl.

A further aspect of the invention relates to novel compounds of the formula IV (IV)

where R1 and R2 are the same or different and are each independently
1) —$(C_6$-$C_{14})$-aryl where aryl is unsubstituted or mono-, di- or trisubstituted independently by R11,
where R11 is
a) F, Cl, I or Br,
b) —$(C_1$-$C_4)$-alkyl,
c) —CN,
d) —$CF_3$,
e) —$OR^5$ in which $R^5$ is a hydrogen atom or —$(C_1$-$C_4)$-alkyl,
f) —$N(R^5)$—$R^6$ in which $R^5$ and $R^6$ are each independently a hydrogen atom or —$(C_1$-$C_4)$-alkyl,
g) —$C(O)$—$R^5$ in which $R^5$ is a hydrogen atom or —$(C_1$-$C_4)$-alkyl, or
h) —$S(O)_x$—$R^5$ in which x is the integer zero, 1 or 2, and $R^5$ is a hydrogen atom or —$(C_1$-$C_4)$-alkyl, or
2) a 4- to 15-membered Het ring where the Het ring is unsubstituted or mono-, di- or trisubstituted independently by —$(C_1$-$C_5)$-alkyl, —$(C_1$-$C_5)$-alkoxy, halogen, nitro, amino, trifluoro-methyl, hydroxyl, hydroxy-$(C_1$-$C_4)$-alkyl, methylenedioxy, ethylenedioxy, formyl, acetyl, cyano, hydroxycarbonyl, amino-carbonyl or —$(C_1$-$C_4)$-alkoxycarbonyl,
R3 is 1) —$(C_6$-$C_{14})$-aryl in which aryl is unsubstituted or mono-, di- or trisubstituted independently
by —$NO_2$, —O—$(C_1$-$C_4)$-alkyl, F, Cl or bromine,
2) —O—$C(CH_3)_3$, or
3) —O—CH(R7)-aryl in which aryl is unsubstituted or mono-, di- or trisubstituted independently
by —$NO_2$, —O—$CH_3$, F, Cl or bromine,
in which R7 is a hydrogen atom or —$(C_1$-$C_4)$-alkyl,
R4 is 1) a hydrogen atom,
2) —$(C_1$-$C_4)$-alkyl or
3) —CH(R8)-aryl
in which R8 is a hydrogen atom or —$(C_1$-$C_4)$-alkyl.

The invention therefore further relates to a process for obtaining the novel compounds of the formula IV, which comprises
a) hydrogenating the compound of the formula II,
in which R1, R2, R3 and R4 are each as defined in the novel compound of the formula II,
in the presence of hydrogen and a catalyst and converting it to a compound of the formula I, and
b) reacting the resulting compound of the formula I with a tert-butyl dicarbonate and an acylation catalyst such as dimethylaminopyridine (DMAP) to give a compound of the formula IV

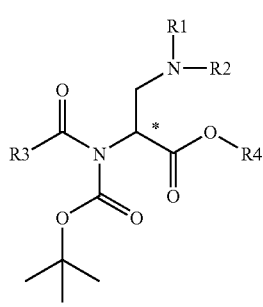

in which R1, R2, R3 and R4 are each as defined in the novel compound of the formula II.

The compounds of the formulae I, II, III and IV are suitable as intermediates for the preparation of IkB kinase inhibitors (WO 01/30774 A1).

The invention is illustrated in detail hereinafter with reference to examples.

End products are generally determined by $^1$H NMR (400 MHz, in DMSO-D6); in each case, the main peak or the two main peaks are reported. Temperatures are reported in degrees Celsius; RT means room temperature (22° C. to 26° C.). Abbreviations used are either explained or correspond to the usual conventions.

EXAMPLES

Example 1

Preparation of methyl 2-benzoylamino-3-diphenylaminoacrylate

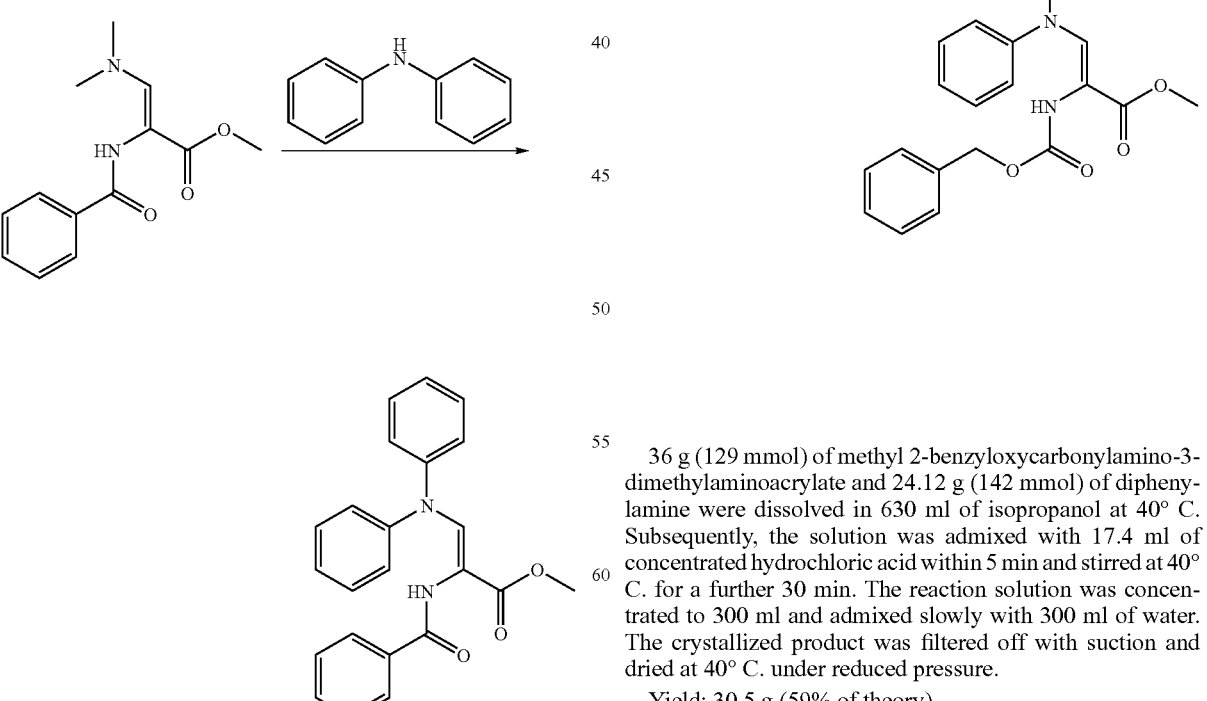

66 g (266 mmol) of methyl 2-benzoylamino-3-dimethylaminoacrylate and 50 g (295 mmol) of diphenylamine were dissolved at 40° C. in 1300 ml of isopropanol. The solution was admixed with 60 ml (725 mmol) of concentrated hydrochloric acid within 5 minutes (min) and stirred for a further 10 min. 550 ml of solvent were evaporated off under reduced pressure, the suspension was cooled to 10° C. and the crystallized product was filtered off.

Yield: 83.5 g (84% of theory)

$^1$H NMR: 3.62 (s, 3H), 6.95-7.10 (m, 6H), 7.20-7.30 (m, 8H), 7.32-7.40 (m, 1H), 7.61 (s, 1H), 8.70 (s, 1H)

Example 2

Preparation of methyl 2-benzyloxycarbonylamino-3-diphenylaminoacrylate 36 g (129 mmol) of methyl 2-benzyloxycarbonylamino-3-dimethylaminoacrylate and 24.12 g (142 mmol) of diphenylamine were dissolved in 630 ml of isopropanol at 40° C. Subsequently, the solution was admixed with 17.4 ml of concentrated hydrochloric acid within 5 min and stirred at 40° C. for a further 30 min. The reaction solution was concentrated to 300 ml and admixed slowly with 300 ml of water. The crystallized product was filtered off with suction and dried at 40° C. under reduced pressure.

Yield: 30.5 g (59% of theory)

$^1$H NMR: 3.62 (s, 3H), 4.68 (s, 2H), 6.95-7.10 (m, 6H), 7.20-7.50 (m, 9H), 7.61 (s, 1H)

Example 3

Preparation of racemic methyl 2-benzoylamino-3-diphenylaminopropionate

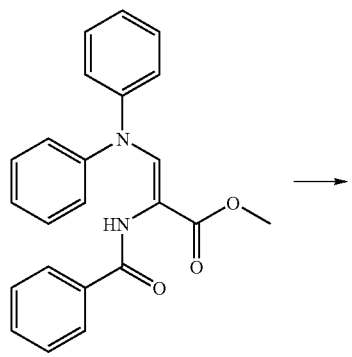

With exclusion of oxygen, an autoclave was charged with 1 g (2.68 mmol) of methyl 2-benzoylamino-3-diphenylaminoacrylate and 40 mg (0.042 mmol) of tris(triphenylphosphine)rhodium(I) chloride. After purging with argon, 40 ml of oxygen-free methanol were added. The autoclave was sealed gas-tight and the solution was hydrogenated at RT for 20 hours (h). The autoclave was decompressed and purged with nitrogen. The solvent was evaporated off under reduced pressure and the residue was chromatographed through a column filled with silica gel 60 (eluent: 1:1 ethyl acetate/heptane). After the solvents had been evaporated off under reduced pressure, a white solid remained, which was utilized for the formulation of a method and as a system test for the determination of the enantiomeric purity by HPLC on chiral phase.

HPLC column: Chiralpak OD 4×250

Eluent: 45:2:1 hexane/EtOH/MeOH+0.1% diethylamine

Temperature: 30° C.

Reactant retention time: 13.2 minutes

S-Isomer retention time: 11.8 minutes

R-Isomer retention time: 14.2 minutes

Yield: 0.5 g (50% of theory)

$^1$H NMR: 3.62 (s, 3H), 4.15-4.35 (m, 2H), 4.75-4.90 (m, 1H), 6.90-7.05 (m, 6H), 7.20-7.30 (m, 4H), 7.40-7.48 (m, 2H), 7.50-7.60 (m, 1H), 7.70-7.78 (d, 2H), 8.85 (d, 1H)

Example 4

Preparation of methyl (S)-2-benzoylamino-3-diphenylaminopropionate

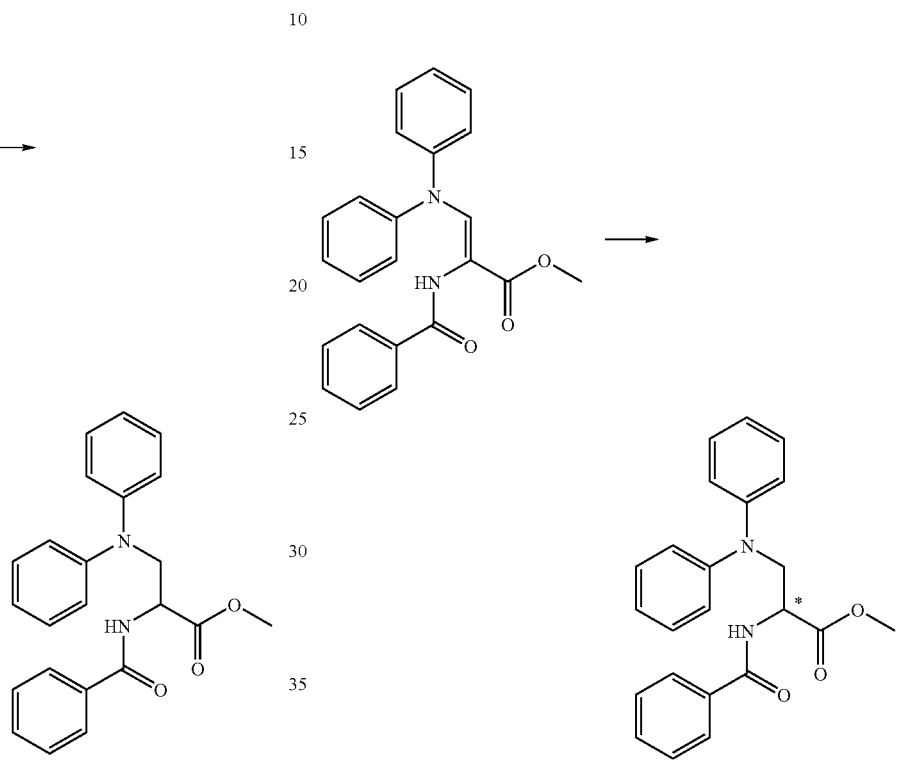

With exclusion of oxygen and moisture, an ampule was charged with 100 mg of methyl 2-benzoylamino-3-diphenylaminoacrylate (0.255 mmol) and 1.9 mg (0.0026 mmol, 0.01 equivalent) of [(S,S)-Et-FerroTANE-Rh]BF$_4$. After purging with argon, 5 ml of oxygen-free methanol were added. The ampule was sealed gas-tight and hydrogenated in an autoclave at 20 bar of hydrogen pressure for 24 h. The autoclave was decompressed and purged with nitrogen. The conversion of the hydrogenation was determined by HPLC. The enantioselectivity was determined by HPLC on chiral phase by the method described in Example 4. The [(R,R)-Et-FerroTANE-Rh]BF$_4$ catalyst afforded the corresponding R derivative in the same yield and enantiomeric purity.

ee: 87%

Example 5

Preparation of methyl (S)- and (R)-2-benzoylamino-3-diphenylaminopropionate

Analogously to Example 4, methyl 2-benzoylamino-3-diphenylaminoacrylate was hydrogenated with various catalysts and solvents. In the case of the catalysts which had not been prepared beforehand, the active catalyst was prepared in situ from the optically active phosphine ligand and equimolar amounts of [Rh(cod)Cl]$_2$ as the rhodium(I) salt. The results are compiled in Table 1 below.

TABLE 1

| RCS | Catalyst/ligand | Rhodium salt | Pressure [bar] | Solvent | Conversion [%] | ee [%] |
|---|---|---|---|---|---|---|
| 1:100 | [(R,R)-Et-FerroTANE-Rh]BF$_4$ [268220-96-8] | no | 20 | Toluene | 97 | 90 |
| 1:100 | [(R,R)-Et-FerroTANE-Rh]BF$_4$ [268220-96-8] | no | 20 | Methanol | 95 | R 87 |
| 1:100 | [(R,R)-Et-FerroTANE-Rh]BF$_4$ [268220-96-8] | no | 20 | Dichloromethane | 97 | 85 |
| 1:100 | [(S,S)-Et-FerroTANE-Rh]BF$_4$ [268220-96-8] | no | 20 | Methanol | 94 | S 86 |
| 1:100 | [(R,R)-Me-DUPHOS-Rh]CF$_3$SO$_3$ [136705-77-6] | no | 20 | Toluene | NC | nd |
| 1:100 | [(R,R)-Me-DUPHOS-Rh]CF$_3$SO$_3$ [136705-77-6] | no | 20 | Methanol | 71 | 90 |
| 1:100 | [(R,R)-Me-DUPHOS-Rh]CF$_3$SO$_3$ [136705-77-6] | no | 20 | Dichloromethane | 65 | 86 |
| 1:100 | (R)-(S)-JOSIPHOS [155806-35-2] | yes | 20 | Toluene | 68 | 36 |
| 1:100 | (R)-(S)-JOSIPHOS [155806-35-2] | yes | 20 | Methanol | 91 | 31 |
| 1:100 | (R)-(S)-JOSIPHOS [155806-35-2] | yes | 20 | Dichloromethane | 82 | 11 |
| 1:100 | L-BPPM-E [61478-28-2] | yes | 20 | Toluene | 21 | 68 |
| 1:100 | L-BPPM-E [61478-28-2] | yes | 20 | Methanol | 80 | 35 |
| 1:100 | L-BPPM-E [61478-28-2] | yes | 20 | Dichloromethane | 5 | 45 |
| 1:100 | (S)-BINAPHANE [544461-38-3] | yes | 20 | Toluene | 37 | 6 |
| 1:100 | (S)-BINAPHANE [544461-38-3] | yes | 20 | Methanol | 31 | 48 |
| 1:100 | (S)-BINAPHANE [544461-38-3] | yes | 20 | Dichloromethane | 19 | 46 |
| 1:100 | (R)-(−)-tert-Ferro [155830-69-6] | yes | 20 | Methanol | 59 | 99 |
| 1:100 | (R)-(−)-Cyclohexyl-Ferro [167416-28-6] | yes | 20 | Methanol | 11 | 99 |
| 1:100 | (R,R)-BDPP [96183-46-9] | yes | 20 | Methanol | NC | nd |
| 1:100 | (S,S)-CHIRAPHOS [64896-28-2] | yes | 20 | Methanol | NC | nd |
| 1:100 | (R,R)-DIOP [32305-98-9] | yes | 20 | Methanol | 5 | 95 |
| 1:100 | (R)-PROPHOS [67884-32-6] | yes | 20 | Methanol | NC | nd |
| 1:100 | (S,S)-NORPHOS [71042-55-2] | yes | 20 | Methanol | NC | nd |
| 1:100 | (R,R)-iPr-DUPHOS [136705-65-2] | yes | 20 | Methanol | 30 | 99 |
| 1:100 | [(R,R)-Et-BPE [136705-62-9] | yes | 20 | Methanol | 62 | 99 |
| 1:100 | [(R,R)-Me-BPE-Rh]CF$_3$SO$_3$ [213343-69-2] | no | 20 | Methanol | 55 | 96 |
| 1:100 | (R)-Me-BOPHOZ [406680-93-1] | yes | 20 | Methanol | NC | nd |
| 1:100 | MonoPhos [157488-65-8] | yes | 20 | Methanol | NC | nd |
| 1:100 | MonoPhos [157488-65-8] | yes | 20 | Dichloromethane | NC | nd |
| 1:100 | MonoPhos [490023-37-5] | yes | 20 | Methanol | NC | nd |
| 1:100 | MonoPhos [490023-37-5] | yes | 20 | Dichloromethane | NC | nd |
| 1:100 | MonoPhos [380230-02-4] | yes | 20 | Methanol | NC | nd |
| 1:100 | MonoPhos [380230-02-4] | yes | 20 | Dichloromethane | NC | nd |

RCS = Molar ratio of catalyst to substrate
NC = No conversion
nd = Not determined
R or S in the "ee [%]" column means the particular R or S enantiomer Example 6

With exclusion of oxygen, an autoclave was charged with the amounts of methyl 2-benzoylamino-3-diphenylaminoacrylate and [(R,R)-Me-DUPHOS—Rh]CF$_3$SO$_3$ specified in Table 1. After purging with argon, the amount of oxygen-free methanol specified below was added. The autoclave was sealed gas-tight and the solution was hydrogenated at 30 bar of hydrogen pressure at RT for 20 h. The autoclave was decompressed and purged with nitrogen. The conversion of the hydrogenation was determined by HPLC. The enantioselectivity was determined by HPLC on chiral phase by the method described in Example 4. The result is shown in Table 2.

TABLE 2

| Catalyst/substrate ratio | Catalyst | Reactant [g] | Conversion [%] | ee [%] |
|---|---|---|---|---|
| 1:1000 | [(R,R)-Me-DUPHOS-Rh]CF$_3$SO$_3$ | 26 | 25 | 87 |

Example 7

With exclusion of oxygen, an autoclave was charged with the amounts of methyl 2-benzoylamino-3-diphenylaminoacrylate and [(S,S)-Et-FerroTANE-Rh]BF$_4$ specified in Table 2. After purging with argon, the amount of oxygen-free methanol specified below was added. The autoclave was sealed gas-tight and the solution was hydrogenated at 30 bar of hydrogen pressure at RT for 20 h. The autoclave was decompressed and purged with nitrogen. The solution was filtered, admixed with the same amount of water at 40° C. and stirred at RT for 2 h. The crystallized product is filtered off with suction and dried to constant weight under reduced pressure at 45° C. The conversion of the hydrogenation was determined by HPLC. The enantioselectivity was determined by HPLC on chiral phase by the method described in Example 4. The result is shown in Table 3.

TABLE 3

| Catalyst/substrate ratio | Catalyst | Reactant [g] | Conversion [%] | ee [%] | Yield [%] |
|---|---|---|---|---|---|
| 1:1000 | [(S,S)-Et-FerroTANE-Rh]BF$_4$ [268220-96-8] | 26 | 98 | 85 | 89 |
| 1:2500 | [(S,S)-Et-FerroTANE-Rh]BF$_4$ [268220-96-8] | 26 | 99 | 84 | 88 |

TABLE 3-continued

| Catalyst/sub-strate ratio | Catalyst | Re-actant [g] | Con-version [%] | ee [%] | Yield [%] |
|---|---|---|---|---|---|
| 1:5000 | [(S,S)-Et-FerroTANE-Rh]BF$_4$ [268220-96-8] | 26 | 98 | 86 | 90 |
| 1:10 000 | [(S,S)-Et-FerroTANE-Rh]BF$_4$ [268220-96-8] | 26 | 73 | 85 | n.i. |
| 1:5000 | [(S,S)-Et-FerroTANE-Rh]BF$_4$ [268220-96-8] | 260 | 98 | 85 | 89 | n.i. = Not isolated

Example 8

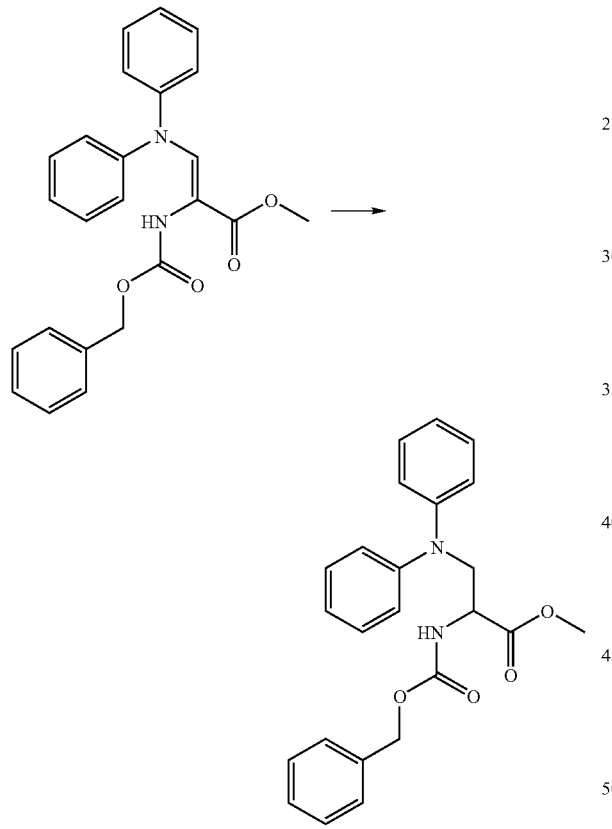

With exclusion of oxygen, an autoclave was charged with 1 g (2.68 mmol) of methyl 2-benzyloxycarbonylamino-3-diphenylaminoacrylate and 40 mg (0.042 mmol) of tris(triphenylphosphine)rhodium(I) chloride. After purging with argon, 40 ml of oxygen-free methanol were added. The autoclave was sealed gas-tight and the solution was hydrogenated at RT for 20 h. The autoclave was decompressed and purged with nitrogen. The solvent was evaporated off under reduced pressure and the residue was purified by means of a column filled with silica gel 60 (eluent: 1:1 ethyl acetate/heptane). After the solvents had been evaporated off under reduced pressure, a white solid remained, which was utilized for the formulation of a method and as a system test for the determination of the enantiomeric purity by HPLC on chiral phase.

| HPLC column: | Chiralpak OD 4 × 250 |
|---|---|
| Eluent: | 50:2:1 hexane/EtOH/MeOH + 0.1% diethylamine |
| Temperature: | 30° C. |
| Reactant retention time: | 19.2 minutes |
| S-Isomer retention time: | 14.6 minutes |
| R-Isomer retention time: | 16.0 minutes |
| Yield: | 0.2 g (20% of theory) |
| 1H NMR: | 3.60 (s, 3H), 3.95-4.15 (m, 2H), 4.35-4.45 (m, 1H), 4.92-5.05 (m, 2H), 6.90-7.00 (m, 6H), 7.15-7.40 (m, 9H), 7.85-7.90 (d, 1H) |

Example 9

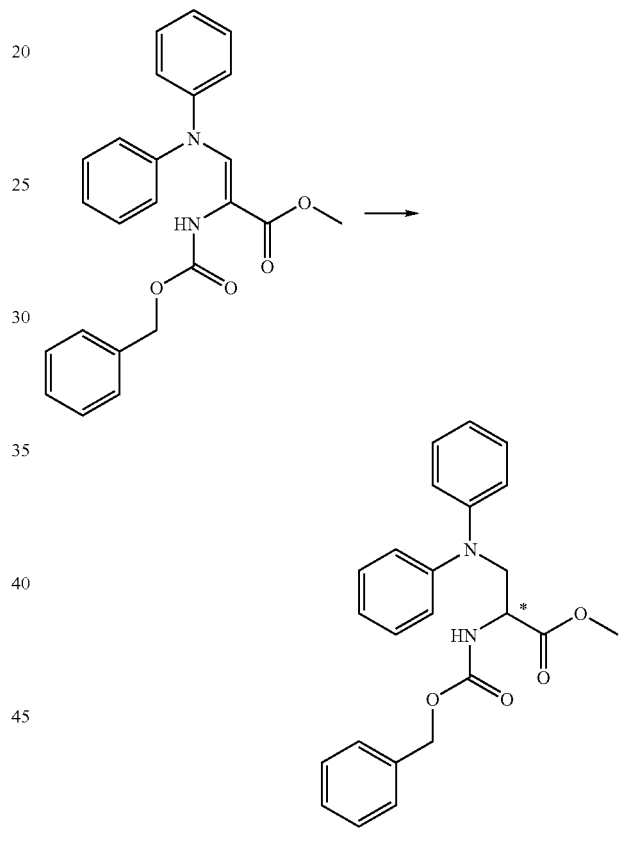

Analogously to Example 5, methyl 2-benzyloxycarbonylamino-3-diphenylaminoacrylate was hydrogenated with various catalysts and solvents. In the case of the catalysts which had not been prepared beforehand, the active catalyst was prepared in situ from the optically active phosphine ligand and equimolar amounts of [Rh(cod)Cl]$_2$ as the rhodium(I) salt. The results are compiled in Table 4 below.

TABLE 4

| RCS | Catalyst/ligand | Rhodium salt | Pressure [bar] | Solvent | Conversion [%] | ee [%] |
|---|---|---|---|---|---|---|
| 1:100 | [(R,R)-Et-FerroTANE-Rh]BF$_4$ [268220-96-8] | no | 20 | Toluene | 15 | 43 |

TABLE 4-continued

| RCS | Catalyst/ligand | Rhodium salt | Pressure [bar] | Solvent | Conversion [%] | ee [%] |
|---|---|---|---|---|---|---|
| 1:100 | [(R,R)-Et-FerroTANE-Rh]BF$_4$ [268220-96-8] | no | 20 | Methanol | 2 | nd |
| 1:100 | [(R,R)-Et-FerroTANE-Rh]BF$_4$ [268220-96-8] | no | 20 | Dichloromethane | 4 | nd |
| 1:100 | [(R,R)-Me-DUPHOS-Rh]CF$_3$SO$_3$ [136705-77-6] | no | 20 | Toluene | 15 | nd |
| 1:100 | [(R,R)-Me-DUPHOS-Rh]CF$_3$SO$_3$ [136705-77-6] | no | 20 | Methanol | 25 | 61 |
| 1:100 | [(R,R)-Me-DUPHOS-Rh]CF$_3$SO$_3$ [136705-77-6] | no | 20 | Dichloromethane | 29 | 46 |
| 1:100 | (R)-(S)-JOSIPHOS [155806-35-2] | yes | 20 | Toluene | 13 | nd |
| 1:100 | (R)-(S)-JOSIPHOS [155806-35-2] | yes | 20 | Methanol | 35 | 28 |
| 1:100 | (R)-(S)-JOSIPHOS [155806-35-2] | yes | 20 | Dichloromethane | 17 | 43 |
| 1:100 | L-BPPM-E [61478-28-2] | yes | 20 | Toluene | 5 | nd |
| 1:100 | L-BPPM-E [61478-28-2] | yes | 20 | Methanol | 7 | nd |
| 1:100 | L-BPPM-E [61478-28-2] | yes | 20 | Dichloromethane | 6 | nd |
| 1:100 | (S)-BINAPHANE [544461-38-3] | yes | 20 | Toluene | <5 | nd |
| 1:100 | (S)-BINAPHANE [544461-38-3] | yes | 20 | Methanol | <5 | nd |
| 1:100 | (S)-BINAPHANE [544461-38-3] | yes | 20 | Dichloromethane | <5 | nd |
| 1:100 | [(R,R)-Me-BPE-Rh]CF$_3$SO$_3$ | no | 20 | Methanol | 36 | 73 |
| 1:100 | (R)-(−)-tert-Ferro [155830-69-6] | yes | 20 | Methanol | 85 | 21 |
| 1:100 | (R)-(S)-JOSIPHOS | yes | 20 | Methanol | 99 | 24 |
| 1:100 | [(R,R)-Et-FerroTANE-Rh]BF$_4$ | yes | 20 | Methanol | 52 | 60 |
| 1:100 | (R,R)-BDPP [96183-46-9] | yes | 20 | Methanol | NC | nd |
| 1:100 | (S,S)-CHIRAPHOS [64896-28-2] | yes | 20 | Methanol | NC | nd |
| 1:100 | (R,R)-DIOP [32305-98-9] | yes | 20 | Methanol | NC | nd |
| 1:100 | (R)-PROPHOS [67884-32-6] | yes | 20 | Methanol | NC | nd |
| 1:100 | (S,S)-NORPHOS [71042-55-2] | yes | 20 | Methanol | NC | nd |
| 1:100 | [(R,R)-Et-BPE-Rh]BF$_4$ | yes | 20 | Methanol | 6 | 23 |
| 1:100 | (R)-Me-BOPHOZ (Eastman) | no | 20 | Methanol | 25 | 16 |

RCS = Ratio of catalyst to substrate;
NC = No conversion
nd = Not determined;
< = Less than

Example 10

Preparation of methyl (S)-2-(benzoyl-tert-butoxycarbonylamino)-3-diphenylaminopropionate

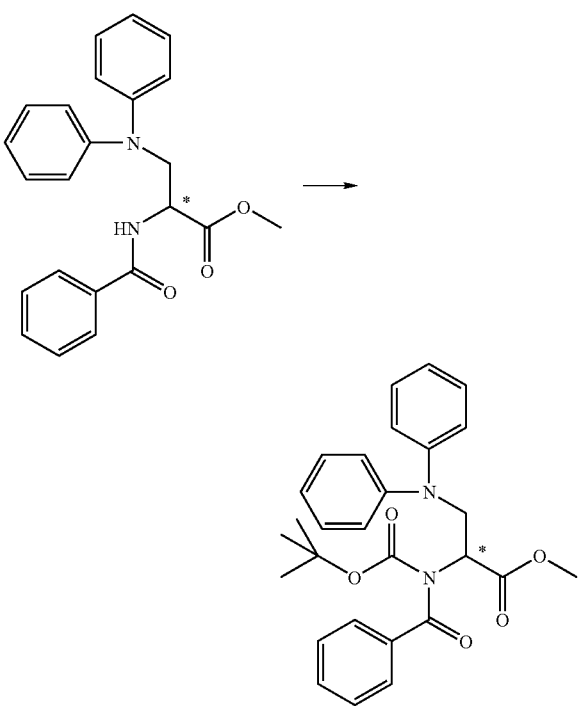

18.7 g of methyl (S)-2-(benzoyl-tert-butoxycarbonylamino)-3-diphenylaminopropionate, ee=85%, 20.6 of di-tert-butyl dicarbonate and 1.2 g of N,N-dimethylaminopyridine were dissolved in 90 ml of acetonitrile and stirred at 40° C. for 3 hours. The acetonitrile was evaporated off under reduced pressure and the remaining residue was taken up in 300 ml of diisopropyl ether and hot-filtered. The product crystallized out overnight as a colorless solid.

Yield: 23.7 g (88% of theory)

$^1$H NMR: 1.38 (s, 9H), 3.70 (s, 3H), 4.35-4.58 (m, 2H), 5.45-5.52 (m, 1H), 6.93-7.05 (m, 6H), 7.13-7.18 (m, 2H), 7.22-7.30 (m, 4H), 7.32-7.30 (m, 2H), 7.45-7.52 (m, 1H)

Example 11

Preparation of methyl (S)-2-(tert-butoxycarbonylamino)-3-diphenylaminopropionate

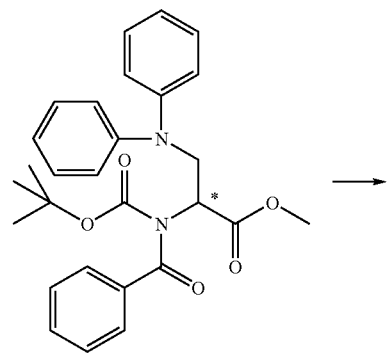

-continued

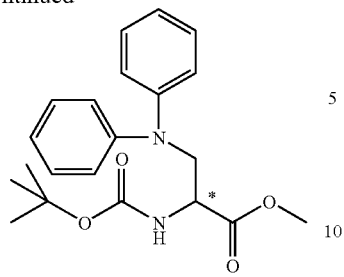

1.3 g of methyl (S)-2-(benzoyl-tert-butoxycarbonylamino)-3-diphenylaminopropionate were dissolved in 13 ml of methanol and admixed with 2.74 ml of a 1M solution of magnesium methoxide in methanol. The solution was stirred at RT overnight and concentrated under reduced pressure. The residue was taken up in ethyl acetate and washed with water. The ethyl acetate phase was dried over sodium sulfate, filtered and concentrated under reduced pressure. The residue was crystallized from a little diisopropyl ether/heptane.

Yield: 0.95 g (90% of theory)

$^1$H NMR: 1.38 (s, 9H), 3.55 (s, 3H), 4.10-4.25 (m, 2H), 4.50-4.62 (m, 1H), 5.10-5.25 (m, 1H), 6.90-7.05 (m, 6H), 7.20-7.30 (m, 4H)

Example 12

Preparation of methyl
(S)-2-amino-3-diphenylaminopropionate
p-toluenesulfonate

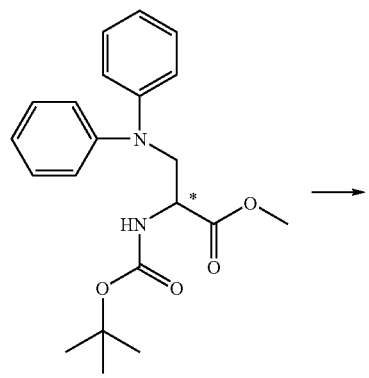

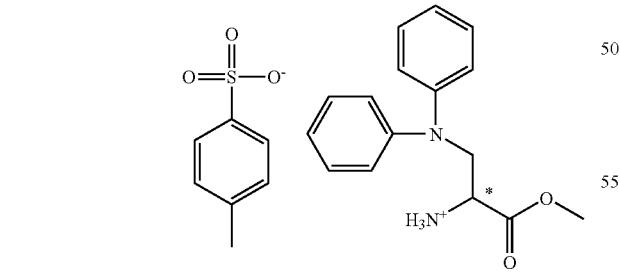

18.5 g of methyl (S)-2-(tert-butoxycarbonylamino)-3-diphenylaminopropionate (ee=85%) were dissolved in 100 ml of dichloromethane and with and admixed with 50 ml of trifluoroacetic acid (TFA). The solution was heated under reflux for 30 minutes and then concentrated to a volume of 100 ml under reduced pressure. The solution was washed with water and admixed with 9 g of p-toluenesulfonic acid. 125 ml of n-butanol were added and the remaining dichloromethane was evaporated off. To crystallize the p-toluenesulfonic salt, the solution was cooled to RT and stirred overnight. The solid was filtered off with suction and dried to constant weight under reduced pressure.

Yield: 16.6 g (81% of theory, based on desired isomer)

$^1$H NMR: 2.38 (s, 3H), 3.30 (s, 3H), 4.10-4.35 (m, 3H), 5.45-5.52 (m, 1H), 6.73-6.95 (m, 6H), 7.01-7.05 (m, 2H), 7.10-7.18 (m, 4H), 7.58-7.62 (m, 2H), 8.30-8.55 (s, broad, 3H, NH)

ee: 99%

Example 13

Preparation of methyl
2-benzoylamino-3-phenylaminoacrylate

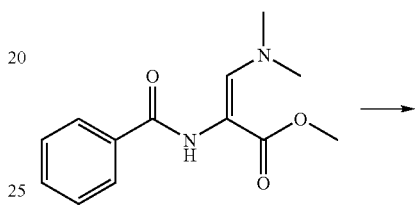

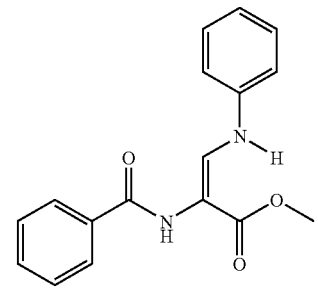

10 g (39.5 mmol) of methyl 2-benzoylamino-3-dimethylaminoacrylate and 11.1 g (118 mmol) of aniline were dissolved at 40° C. in 200 ml of isopropanol. The solution was admixed with 3.6 ml (43.5 mmol) of concentrated hydrochloric acid within 5 minutes (min) and stirred for a further 10 min. 200 ml of deionized water were added, the suspension was cooled to 10° C. and the crystallized product was filtered off.

Yield: 11.5 g (92% of theory)

$^1$H NMR: 3.62 (s, 3H); 6.90-7.00 (m, 1H); 7.19 (d, 2H); 7.25-7.30 (m, 2H); 7.48-7.61 (m, 3H); 7.93 (d, 1H); 8.02 (d, 2H); 8.90 (d, 1H); 9.15 (s, 1H)

Example 14

Preparation of methyl
2-benzoylamino-3-(4-fluorophenylamino)acrylate

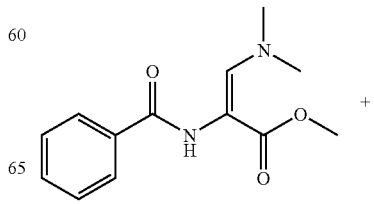 +

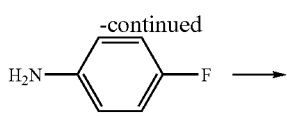

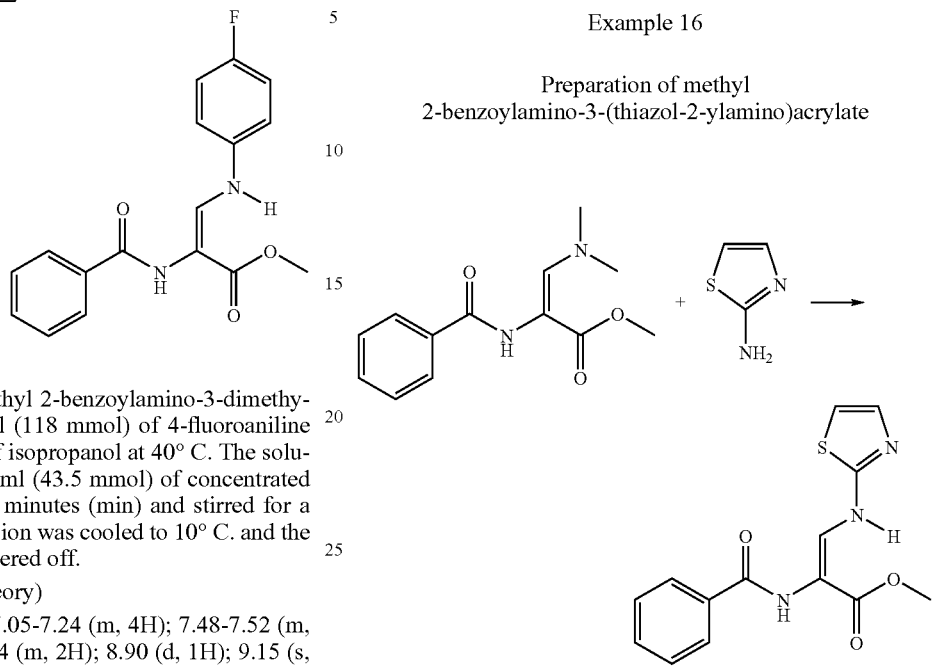

10 g (39.5 mmol) of methyl 2-benzoylamino-3-dimethylaminoacrylate and 11.4 ml (118 mmol) of 4-fluoroaniline were dissolved in 200 ml of isopropanol at 40° C. The solution was admixed with 3.6 ml (43.5 mmol) of concentrated hydrochloric acid within 5 minutes (min) and stirred for a further 30 min. The suspension was cooled to 10° C. and the crystallized product was filtered off.

Yield: 12.4 g (94% of theory)

$^1$H NMR: 3.62 (s, 3H); 7.05-7.24 (m, 4H); 7.48-7.52 (m, 3H); 7.88 (d, 1H); 8.00-8.04 (m, 2H); 8.90 (d, 1H); 9.15 (s, 1H)

Example 15

Preparation of methyl 2-benzoylamino-3-(pyridin-2-ylamino)acrylate

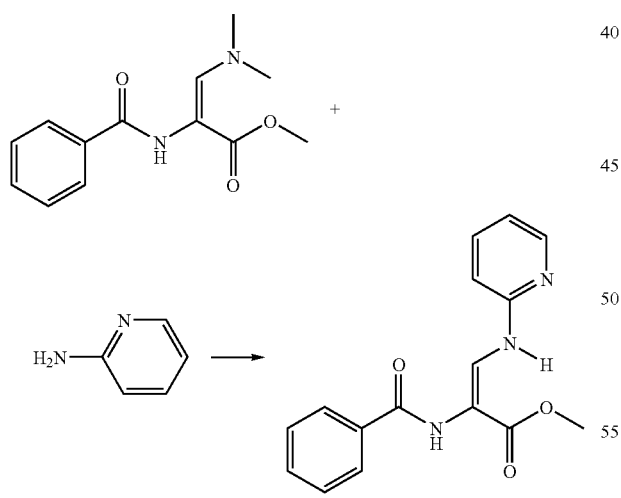

10 g (39.5 mmol) of methyl 2-benzoylamino-3-dimethylaminoacrylate and 11.3 g (118 mmol) of 2-aminopyridine were dissolved in 200 ml of isopropanol at 40° C. The solution was admixed with 3.96 ml (48 mmol) of concentrated hydrochloric acid within 5 minutes (min) and stirred for a further 30 min. The suspension was cooled to 10° C. and the crystallized product was filtered off.

Yield: 7.3 g (60% of theory)

$^1$H NMR: 3.62 (s, 3H); 6.92-6.97 (m, 1H); 7.02 (d, 1H); 7.45-7.70 (m, 4H); 8.02 (d, 2H); 8.22-8.24 (m, 1H); 8.60 (d, 1H); 9.22 (s, 1H); 9.45 (d, 1H)

Example 16

Preparation of methyl 2-benzoylamino-3-(thiazol-2-ylamino)acrylate

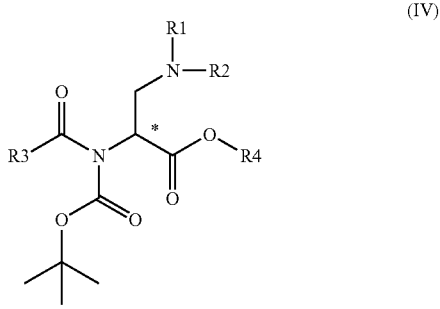

10 g (39.5 mmol) of methyl 2-benzoylamino-3-dimethylaminoacrylate and 11.3 g (118 mmol) of 2-aminothiazole were dissolved at 40° C. in 200 ml of isopropanol. The solution was admixed with 3.96 ml (48 mmol) of concentrated hydrochloric acid within 5 minutes (min) and stirred for a further 60 min. 75 ml of deionized water were added, the suspension was cooled overnight and the crystallized product was filtered off.

Yield: 8.6 g (70% of theory)

$^1$H NMR: 3.62 (s, 3H); 7.08 (d, 1H); 7.32 (d, 1H); 7.45-7.60 (m, 3H); 8.02 (d, 2H); 8.22 (d, 1H); 9.28 (s, 1H); 10.45 (d, 1H)

What is claimed is:

1. A compound of the formula IV:

(IV)

where:

R1 and R2 are the same or different and are each independently:

—($C_6$-$C_{14}$)-aryl where aryl is unsubstituted or mono-, di- or trisubstituted independently by R11, where R11 is
F, Cl, I or Br,
—$(C_1-C_4)$-alkyl,
—CN,
—$CF_3$,
—$OR^5$ in which $R^5$ is a hydrogen atom or —$(C_1-C_4)$-alkyl,
—$N(R^5)$—$R^6$ in which $R^5$ and $R^6$ are each independently a hydrogen atom or —$(C_1-C_4)$-alkyl,
—$C(O)$—$R^5$ in which $R^5$ is a hydrogen atom or —$(C_1-C_4)$-alkyl, or
—$S(O)_x$—$R^5$ in which x is the integer zero, 1 or 2, and $R^5$ is a hydrogen atom or —$(C_1-C_4)$-alkyl, or
R1 and/or R2 are a 4- to 15-membered Het ring where the Het ring is unsubstituted or mono-, di- or trisubstituted independently by —$(C_1-C_5)$-alkyl, —$(C_1-C_5)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxycarbonyl, aminocarbonyl or —$(C_1-C_4)$-alkoxycarbonyl;
R3 is: —$(C_6-C_{14})$-aryl in which aryl is unsubstituted or mono-, di- or
trisubstituted independently by —$NO_2$, —O—$(C_1-C_4)$-alkyl, F, Cl or bromine;
or
—O—CH(R7)-aryl in which aryl is unsubstituted or mono-, di- or
trisubstituted independently by —$NO_2$, —O—$CH_3$, F, Cl or bromine,
in which R7 is a hydrogen atom or —$(C_1-C_4)$-alkyl;
R4 is: a hydrogen atom;
—$(C_1-C_4)$-alkyl; or
—CH(R8)-aryl
in which R8 is a hydrogen atom or —$(C_1-C_4)$-alkyl.

2. A process for obtaining the compound of the formula IV:

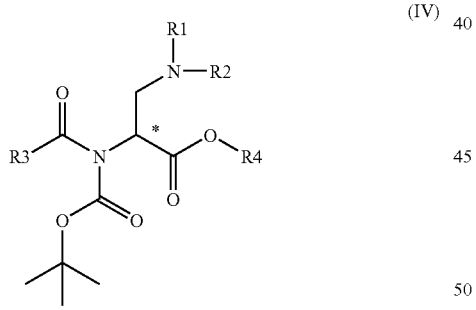

as claimed in claim 1,
where:
R1 and R2 are the same or different and are each independently:
—$(C_6-C_{14})$-aryl where aryl is unsubstituted or mono-, di- or trisubstituted independently by R11,
where R11 is
F, Cl, I or Br,
—$(C_1-C_4)$-alkyl,
—CN,
—$CF_3$,
—$OR^5$ in which $R^5$ is a hydrogen atom or —$(C_1-C_4)$-alkyl,
—$N(R^5)$—$R^6$ in which $R^5$ and $R^6$ are each independently a hydrogen atom or —$(C_1-C_4)$-alkyl;
—$C(O)$—$R^5$ in which $R^5$ is a hydrogen atom or —$(C_1-C_4)$-alkyl; or
—$S(O)_x$—$R^5$ in which x is the integer zero, 1 or 2, and $R^5$ is a hydrogen atom or —$(C_1-C_4)$-alkyl; or
R1 and/or R2 are a 4- to 15-membered Het ring where the Het ring is unsubstituted or mono-, di- or trisubstituted independently by —$(C_1-C_5)$-alkyl, —$(C_1-C_5)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxycarbonyl, aminocarbonyl or —$(C_1-C_4)$-alkoxycarbonyl;
R3 is: —$(C_6-C_{14})$-aryl in which aryl is unsubstituted or mono-, di- or trisubstituted independently by —$NO_2$, —O—$(C_1-C_4)$-alkyl, F, Cl or bromine;
or
—O—CH(R7)-aryl in which aryl is unsubstituted or mono-, di- or trisubstituted independently by —$NO_2$, —O—$CH_3$, F, Cl or bromine,
in which R7 is a hydrogen atom or —$(C_1-C_4)$-alkyl;
R4 is: a hydrogen atom;
—$(C_1-C_4)$-alkyl; or
—CH(R8)-aryl
in which R8 is a hydrogen atom or —$(C_1-C_4)$-alkyl,
said process comprising the step of:
a) hydrogenating the compound of the formula II:

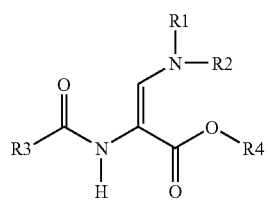

where:
R1 and R2 are the same or different and are each independently:
—$(C_6-C_{14})$-aryl where aryl is unsubstituted or mono-, di- or trisubstituted independently by R11,
where R11 is
F, Cl, I or Br,
—$(C_1-C_4)$-alkyl,
—CN,
—$CF_3$,
—$OR^5$ in which $R^5$ is a hydrogen atom or —$(C_1-C_4)$-alkyl,
—$N(R^5)$—$R^6$ in which $R^5$ and $R^6$ are each independently a hydrogen atom or —$(C_1-C_4)$-alkyl;
—$C(O)$—$R^5$ in which $R^5$ is a hydrogen atom or —$(C_1-C_4)$-alkyl; or
—$S(O)_x$—$R^5$ in which x is the integer zero, 1 or 2, and $R^5$ is a hydrogen atom or —$(C_1-C_4)$-alkyl; or
$R^1$ and/or $R^2$ are a 4- to 15-membered Het ring where the Het ring is unsubstituted or mono-, di- or trisubstituted independently by —$(C_1-C_5)$-alkyl, —$(C_1-C_5)$-alkoxy, halogen, nitro, amino, trifluoromethyl, hydroxyl, hydroxy-$(C_1-C_4)$-alkyl, methylenedioxy, ethylenedioxy, formyl, acetyl, cyano, hydroxycarbonyl, aminocarbonyl or —$(C_1-C_4)$-alkoxycarbonyl;
R3 is: —$(C_6-C_{14})$-aryl in which aryl is unsubstituted or mono-, di- or trisubstituted independently by —$NO_2$, —O—$(C_1-C_4)$-alkyl, F, Cl or bromine;

or

—O—CH(R7)-aryl in which aryl is unsubstituted or mono-, di- or trisubstituted independently by —NO$_2$, —O—CH$_3$, F, Cl or bromine, in which R7 is a hydrogen atom or —(C$_1$-C$_4$)-alkyl;

R4 is: a hydrogen atom;

—(C$_1$-C$_4$)-alkyl; or

—CH(R8)-aryl in which R8 is a hydrogen atom or —(C$_1$-C$_4$)-alkyl, in the presence of hydrogen and a catalyst to convert the compound of formula II to a compound of formula I;

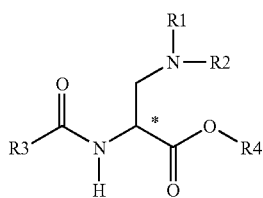

(I)

and b) reacting the compound of formula I with a tert-butyl dicarbonate and an acylation catalyst to provide a compound of said formula IV.

3. The compound of claim 1, wherein said aryl for R1, R2, and R3 is unsubstituted.

4. The compound of claim 1, wherein R3 is —(C$_6$-C$_{14}$)-aryl in which aryl is unsubstituted or mono-, di- or tri-substituted, independently, by groups selected from —NO$_2$, —O—(C$_1$-C$_4$)-alkyl, F, Cl and bromine.

5. The compound of claim 4, wherein said aryl for R3 is unsubstituted.

6. The compound of claim 4, wherein said —(C$_6$-C$_{14}$)-aryl for R3 is phenyl, which is unsubstituted or mono-, di- or tri-substituted, independently, by groups selected from —NO$_2$, —O—(C$_1$-C$_4$)-alkyl, F, Cl and bromine.

7. The compound of claim 6, wherein said phenyl is unsubstituted.

8. The compound of claim 1, wherein R1 and R2 are the same or different and are each independently:

—(C$_6$-C$_{14}$)-aryl where aryl is unsubstituted or mono-, di- or tri-substituted independently by R11, where R$^{11}$ is F, Cl, I or Br, —(C$_1$-C$_4$)-alkyl,

—CN,

—CF$_3$,

—OR$^5$ in which R$^5$ is a hydrogen atom or —(C$_1$-C$_4$)-alkyl,

—N(R$^5$)—R$^6$ in which R$^5$ and R$^6$ are each independently a hydrogen atom or —(C$_1$-C$_4$)-alkyl, —C(O)—R$^5$ in which R$^5$ is a hydrogen atom or —(C$_1$-C$_4$)-alkyl, or —S(O)$_x$—R$^5$ in which x is zero, 1 or 2, and R$^5$ is a hydrogen atom or —(C$_1$-C$_4$)-alkyl.

9. The compound of claim 8, wherein said —(C$_6$-C$_{14}$)-aryl for R1 and R2 is unsubstituted.

10. The compound of claim 8, wherein said —(C$_6$-C$_{14}$)-aryl for R1 and R2 is phenyl, which can be substituted or unsubstituted.

11. The compound of claim 10, wherein said phenyl is unsubstituted.

12. The compound of claim 11, wherein R3 is —(C$_6$-C$_{14}$)-aryl in which aryl is unsubstituted or mono-, di- or tri-substituted, independently, by groups selected from —NO$_2$, —O—(C$_1$-C$_4$)-alkyl, F, Cl and bromine.

13. The compound of claim 12, wherein said —(C$_6$-C$_{14}$)-aryl for R3 is unsubstituted.

14. The compound of claim 13, wherein said —(C$_6$-C$_{14}$)-aryl for R3 is phenyl.

15. The compound of claim 14, wherein R4 is —(C$_1$-C$_4$)-alkyl.

16. The compound of claim 15, wherein the compound is (S)-2-(benzoyl-tert-butoxycarbonylamino)-3-diphenylaminopropionate, which corresponds to the following structural formula:

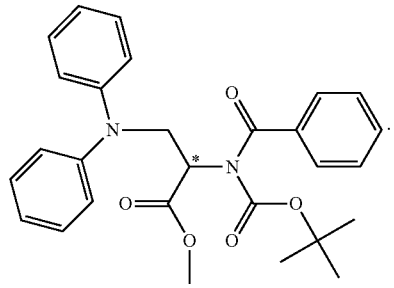

* * * * *